(12) United States Patent
Glatz et al.

(10) Patent No.: US 11,596,373 B2
(45) Date of Patent: Mar. 7, 2023

(54) MEDICAL IMAGING APPARATUS PROVIDING AR-SUPPORT

(71) Applicant: Brainlab AG, Munich (DE)

(72) Inventors: Florian Glatz, Kaufering (DE); Ralf Schwitzko, Holzkirchen (DE); Michael Bertram, Markt Schwaben (DE)

(73) Assignee: Brainlab AG, Munich (DE)

( * ) Notice: Subject to any disclaimer, the term of this patent is extended or adjusted under 35 U.S.C. 154(b) by 333 days.

(21) Appl. No.: 17/056,145

(22) PCT Filed: Jul. 31, 2018

(86) PCT No.: PCT/EP2018/070749
§ 371 (c)(1),
(2) Date: Nov. 17, 2020

(87) PCT Pub. No.: WO2020/025110
PCT Pub. Date: Feb. 6, 2020

(65) Prior Publication Data
US 2021/0212644 A1   Jul. 15, 2021

(51) Int. Cl.
*A61B 5/00*   (2006.01)
*A61B 18/18*  (2006.01)
(Continued)

(52) U.S. Cl.
CPC ............... *A61B 6/466* (2013.01); *A61B 6/04* (2013.01); *A61B 6/06* (2013.01); *A61B 6/4064* (2013.01);
(Continued)

(58) Field of Classification Search
CPC ............ G06T 2207/10121; G06T 7/30; G06T 19/006; G06T 7/70; G06T 19/003; G06T 2200/04; G06T 13/40; G06T 15/10; G06T 7/60; G06T 2210/41; G06T 2219/2016; G06T 17/00; G06T 19/00;
(Continued)

(56) References Cited

U.S. PATENT DOCUMENTS 6,554,472 B1   4/2003   Dietz et al.
9,892,564 B1   2/2018   Cvetko et al.
(Continued)

FOREIGN PATENT DOCUMENTS

DE   10 2013 215 516 A1   2/2015
EP              2119397 A1   11/2009
(Continued)

OTHER PUBLICATIONS

International Search Report and Written Opinion for corresponding International Application No. PCT/EP2018/070749, dated Apr. 11, 2019. 9 pages.
(Continued)

*Primary Examiner* — Don K Wong
(74) *Attorney, Agent, or Firm* — Tucker Ellis LLP (57) ABSTRACT

Provided is a medical imaging apparatus having an AR-visualization module operably coupled to a camera and to a position determination module, which is adapted to create an AR-image based on an image received from the camera and an AR-overlay positionally registered with the image, and which includes a display interface adapted to transmit the created AR-image to a medical display.

20 Claims, 5 Drawing Sheets

(51) Int. Cl.
*A61B 6/00* (2006.01)
*A61B 90/00* (2016.01)
*A61B 6/04* (2006.01)
*A61B 6/06* (2006.01)

(52) U.S. Cl.
CPC ............ *A61B 6/4405* (2013.01); *A61B 90/36* (2016.02); *A61B 2090/365* (2016.02)

(58) Field of Classification Search
CPC ....... G06T 2207/30004; G06T 2200/24; G06T 3/4007; G06T 7/0012; G06T 2215/12; G06T 1/0007; G06T 7/187; G03B 15/14; A61N 2005/1061; G06F 3/011; G06F 3/0346; G06F 2/0304; G06F 3/147; G06F 3/14; G06F 3/0484; G06F 3/04886; G06F 3/0321; G02B 2027/0185; G02B 6/0011; G02B 21/36; G02B 2027/0123; G02B 2027/0125; G02B 5/1823; G06V 20/20; G06V 20/653; G06V 20/80; G06V 20/647; G06V 2201/034; G06V 40/161; H04N 13/351; H04N 13/279; H04N 5/225

See application file for complete search history.

(56) References Cited

U.S. PATENT DOCUMENTS

| | | |
|---|---|---|
| 2009/0285366 A1 | 11/2009 | Essenreiter et al. |
| 2010/0012519 A1 | 1/2010 | Feldman et al. |
| 2010/0016083 A1 | 1/2010 | Bruce |
| 2017/0119329 A1 | 5/2017 | Warner |
| 2017/0215823 A1 | 8/2017 | Alekseyevich et al. |
| 2019/0110685 A1* | 4/2019 | Pautsch ................. A61B 34/20 |

FOREIGN PATENT DOCUMENTS

| | | |
|---|---|---|
| EP | 2 687 159 B1 | 1/2014 |
| EP | 3318214 A1 | 5/2018 |

OTHER PUBLICATIONS

Christoph Bichlmeier, Dissertation TU Munich 2010 "Immersive, Interactive and Contextual In-Situ Visualization for Medical Applications".

Video in Youtube form Mar. 9, 2018 https://www.youtube.com/watch?v=Hmho-EdWxMY&t=72s Visionary—B CV: Effective 3D collision warning assistance from SICK | SICK AG.

DOI10.5152/dir.2017.16323 "1.5 T augmented reality navigated interventional MRI: paravertebral sympathetic plexus injections" David R. Marker, Apr. 18, 2017.

Roger Y. Tsai, "An Efficient and Accurate Camera Calibration Technique for 3D Machine Vision", Proceedings of the IEEE Conference on Computer Vision and Pattern Recognition. Miami Beach, Florida, 1986, pp. 364-374.

Roger Y. Tsai, "A Versatile Camera Calibration Technique for High-Accuracy 3D Machine Vision Metrology Using Off-the-Shelf TV Cameras and Lenses", IEEE Journal of Robotics and Automation, vol. RA-3, No. 4, Aug. 1987, pp. 323-344.

Ziv Yaniv, "Fluoroscopic X-ray Image Processing and Registration for Computer-Aided Orthopedic Surgery". Oct. 1, 1998.

* cited by examiner

MEDICAL IMAGING APPARATUS PROVIDING AR-SUPPORT

RELATED APPLICATION DATA

This application is a national phase application of International Application No. PCT/EP2018/070749 filed Jul. 31, 2018, the contents of which are incorporated herein by reference.

FIELD OF THE INVENTION

The present invention relates to a medical imaging apparatus that provides images of a patient, particularly fluoroscopic images of a patient. The present invention further relates to a corresponding method involving the use of such imaging apparatus and a corresponding computer program that causes a computer to perform such method.

TECHNICAL BACKGROUND

For obtaining medical images of a patient, a wide variety of imaging apparatus and devices is known and used in a large number of medical appliances. A specific type of such devices involves the use of computed tomography (CT) or cone-beam computed tomography (CBCT), for which a beam of radiation is generated between a radiation emitter and a radiation detector, that passes through the patient's anatomy. The transmitted radiation is received by the detector and a computer calculates at least one 2D- or 3D-radiographic image from the signals received from the detector.

For example, EP 2 687 159 A1 discloses a patient positioning and imaging system that has two rotatable rings carrying a radiation source and a radiation detector. The radiation source and the radiation detector are thus movable around a patient lying on the patient couch of the imaging system.

The present invention has the object of facilitating the use of such imaging device, particularly in the context of setting up the imaging device with respect to the patient.

This object is solved by the subject-matter of independent claims 1, 13, and 14. The dependent claims define specific embodiments of the present invention.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

The present invention relates to medical imaging apparatus having an AR-visualization module operably coupled to a camera and to a position determination module, which is adapted to create an AR-image based on an image received from the camera and an AR-overlay positionally registered with the image, and which includes a display interface adapted to transmit the created AR-image to a medical display. The present invention further relates to a corresponding method and a corresponding computer program for presenting an AR-image that is based on an image received from the camera and an AR-overlay positionally registered with the image.

GENERAL DESCRIPTION OF THE INVENTION

In this section, a description of the general features of the present invention is given for example by referring to possible embodiments of the invention.

In general, the invention reaches the aforementioned object by providing, in a first aspect, a medical imaging apparatus that comprises:
- a radiation emitter movably supported by a first support structure along a first annular pathway;
- a radiation detector movably supported by a second support structure along a second annular pathway;
- a camera positionally coupled to and moving together with either the radiation emitter or the radiation detector, and oriented towards an area surrounded by the first and the second pathway;
- a position determination module adapted to determine the spatial position of a radiation beam stretching between the radiation emitter and the radiation detector;
- an AR-visualization module operably coupled to the camera and to the position determination module, which is adapted to create an AR-image based on an image received from the camera and an AR-overlay positionally registered with the image, and which includes a display interface adapted to transmit the created AR-image to a medical display.

In other words, the present imaging device is adapted to provide additional visual information to medical personnel, wherein this additional information comprises, on the one hand, a camera image obtained from a camera that aims substantially at an observation area where the radiation beam crosses the anatomy of a patient around whom the radiation emitter and the radiation detector are movably supported. On the other hand, the additional information provided by the inventive imaging apparatus comprises an augmented reality (AR) overlay. By superimposing the AR-overlay with the camera image in a positionally correct location, an AR-image is obtained which is then transmitted to a display interface of the imaging device to be eventually displayed by a medical display which is operably connected to the imaging device via the display interface.

For example, the provided AR-image may comprise an AR-overlay that shows the field of view that is possible with the current setup or the radiation emitter and the radiation detector. As the AR-overlay is shown in a positionally correct alignment with the camera image, medical personnel can immediately tell by looking at the display, which areas and parts of the patient's anatomy will be depicted on a radioscopic image obtained with the current setup of the medical imaging apparatus. For example, the displayed field of view changes its size, its position with respect to the patient's anatomy and/or its shape as soon as the actual relative position between the radiation emitter, the radiation detector and the patient's anatomy is altered and the shape of the collimator of the radiation emitter is altered, respectively, in correspondence with a new setup of the imaging apparatus.

Thus, the present invention allows for a precise planning which parts of the patient's anatomy are radiated by the radiation beam during a later image acquisition.

The provided AR-image may also contain an AR-overlay that shows any desirable image data in a registered and therefore positionally aligned manner with respect to the camera image. By doing so, medical personnel can actually see at which position inner structures of the patient's anatomy lie underneath the patient's skin. The image within the AR-overlay may be derived from or actually be one or more previously acquired 2D- or 3D-images of the patient, or may depict positional guidelines that are to help in handling an instrument with respect to the patient's anatomy. For example, the content of the AR-overlay can be reconstructed from a 3D-image-dataset (CT, CBCT, MRI) of the patient's anatomy, wherein the displayed AR-overlay always shows a reconstructed 2D-image which plane is perpendicular to the viewing direction of the camera and is therefore parallel to the plane of the camera image. Further, as soon as the camera is moved with respect to the patient's anatomy, the reconstructed 2D-image changes in correspondence with the changed viewing direction of the camera and the corresponding plane of the camera image.

Specifically, any of the following content may be shown by the AR-overlay:
- a radioscopic-image obtained from the radiation detector, particularly a currently acquired and/or a previously acquired radioscopic-image;
- a reconstructed-radioscopic-image calculated from currently acquired and/or previously acquired radioscopic-images of the patient;
- a 2D-image of the patient;
- a 3D-image-dataset of the patient;
- a 2D-image calculated from a 3D-image-dataset of the patient;
- a virtual 2D- or 3D-representation of anatomical structures of a patient, particularly of pathological structures of the patient;
- a virtual 2D- or 3D-representation of a predefined planning geometry, which in particular contains a trajectory, a target point and/or an entry point for an instrument;
- a virtual representation of the field-of-view of the imaging unit comprising the radiation emitter and the radiation detector;
- a virtual representation of the radiation beam;
- a virtual representation of an area of the patient's skin and/or a volume of the patient's body that is intersected by the radiation beam.

As previously described, both, the radiation emitter and the radiation detector are movably supported by respective support structures along annular pathways, which extend around a volume that a patient is or will be positioned in. In order to ensure that the radiation detector always receives the radiation emitted by the radiation emitter, common CT-imaging devices require a rigid coupling between the radiation emitter and the radiation detector, such that when the radiation emitter and the radiation detector are moved around the patient, the radiation beam always runs through the same center point. The inventive imaging device however may comprise a radiation emitter and a radiation detector that are movably supported with respect to each other in an independent manner, such that the radiation beam is not tied to such center point but may rather be offset from the center point around which the radiation emitter and the radiation detector are moved.

Specifically, the first support structure and the second support structure may be formed as support "rings" which run around the volume the patient is positioned in. The radiation emitter and the radiation detector may therefore be moved around a common center point or common axis of rotation, but do not need to be positioned at exact opposite sides of the center point or axis of rotation. Rather, the radiation emitter and radiation detector may be moved towards each other along the pathways as long as it can be assured that the radiation emitted from the radiation emitter reaches (only) the radiation detector. Consequently, additional degrees of freedom are obtained for arranging the radiation beam with respect to the patient's anatomy by "shifting" the beam away from the center point or axis of rotation.

Further, the position determination module of the imaging device may determine the spatial position of the radiation beam with respect to the patient's anatomy by receiving signals from one or more sensors that determine the spatial position of the radiation emitter and/or the spatial position of the radiation detector and/or the shape of the radiation emitter collimator. In the alternative, at least the signals of the position sensing sensors may be supplemented or even substituted by the use of an optical, magnetic or ultrasound tracking system, all of which are well known and widely used in the art to determine the spatial position of objects with respect to each other.

Moreover, the inventive medical imaging apparatus may further comprise an undercarriage having a plurality of wheels, which allow the imaging apparatus to freely move in two dimensions over the ground, and in particular with respect to a patient table provided separately to the medical imaging apparatus.

In other words, the imaging device according to the present invention may be a "mobile" or "transportable" imaging apparatus which can be easily transferred from one location to another. For example, the imaging device may have one or more handles for being grabbed by a person who manually pushes or otherwise moves the imaging apparatus over the ground. Alternatively or additionally to such handle, the imaging device may also comprise a motorized drive which is controlled via a user interface, for example a control panel which is either provided as a separate remote control or as unit which is integrated within the imaging device. For the purpose of mobility, the undercarriage may have a plurality of wheels or rollers. In this respect, it is further possible to move the imaging apparatus with respect to the patient table which may be a stationary installation in an operating, diagnostic or treatment room of a hospital.

In order to display the created AR-image, the imaging device may further comprise one or more display devices connected to the display interface.

At least one first display device may be positionally coupled to and moving together with either the radiation emitter or the radiation detector, and may further be oriented away from the area surrounded by the first and the second pathways. In other words, the housing for the radiation emitter or the housing for the radiation detector may have at least one display, for example a TFT-monitor, that displays the created AR-image. In case any of those housing comprises both, the camera and the display, the housing may be sort of "see-through", since the display on one side of the housing shows the very image that is delivered by the camera on the opposite side of the housing. In this case, the display may be even seen as a "window" through the housing. Of course, the camera image may be manipulated. For example, the camera-display-arrangement may be used as a "magnifying glass", such that anatomical structures within the cameras field of view are easier to observe on the display. Further, the camera as well as the display may be moved around the patient along with a respective housing for the radiation emitter or radiation detector, such that medical personnel are able to obtain images from different viewing angles. Additionally or alternatively to the aforementioned display, the imaging device may be constituted by any conceivable kind of mobile display which is freely movable with respect to the imaging device. For example, such display may be part of a tablet computer or smartphone, or may be provided as AR-spectacles/AR-goggles. Further, the created AR-image may be displayed by any of those movable displays as soon as the display that is connected to either the emitter housing or the detector housing is moved around the patient and reaches a position where it cannot be looked at. Basically, looking at a display that is positioned right above or underneath the patient is impossible, and it becomes more and more inconvenient to look at the display the more it is oriented in a vertical direction.

In case the imaging device is "movable"/"transportable" over ground and in two dimensions, just as described above, the medical device may further be adapted to be transferred into a transport configuration. In this transport configuration, the camera may be oriented towards an area which would otherwise not be observable by a user who moves the imaging device from one place to another. In this case, the camera that is normally oriented towards a patient now has a second function, which is that of a "reversing camera". With the obtained camera image being shown to the user, possible blind spots in the user's field of view are now observable such that damage to the imaging device and other medical appliances that may occur during transport can be effectively avoided. Further, the display attached to either the radiation emitter housing or the radiation detector housing may be moved to a basically horizontal, preferably tilted slightly upwards towards the user's face, so as to directly show the camera image to the user. Further, the AR-overlay may contain visual aids that help the user in maneuvering and positioning the imaging device. For example, the dimensions of the imaging device can be visually shown in the AR-overlay, such that the user may for example immediately see in the image whether or not it is possible to pass a certain obstacle, such as walls, doorframes or objects on the floor of the hospital.

In a further embodiment of the present invention, the imaging device is adapted to control the radiation emitter, particularly an initial size, initial shape and/or initial spatial position of the radiation beam in accordance with a pattern recognition procedure performed on an image that is provided by the camera, particularly in accordance with a size, a shape and/or a spatial position of a surgical site as seen in the camera image, which is left uncovered by a surgical drape. For example, a surgical site is left uncovered by a surgical drape having a certain and uniform color. While surgery progresses, the surgeon may wish to check the current status of surgery by making images with the imaging device. This however would not only require positioning the imaging device with respect to the surgical site, but also to set up the spatial position and shape of the radiation beam in order to avoid excessive and unnecessary exposure of the patient tissue to radiation. In order to facilitate setting up the beam geometry with respect to the patient, the shape of the uncovered surgical site may be automatically detected within the camera image, wherein on this basis, an "initial" setup for the beam geometry with respect to the patient can be suggested and shown on the display. For example, the initial setup may suggest that the beam is restricted to the uncovered parts of the patient's anatomy and extends within a predefined angular range with respect to the patient's skin or "uncovered plane", whereupon the surgeon can of course further adjust the beam geometry as desired.

A further aspect of the present invention refers to a method that involves the use of any of the above described imaging apparatus, wherein an AR-image is generated on the basis of a camera image and on an AR-overlay, which is then shown to a user on a medical display.

Specifically, such method may comprise any of the following steps:
positioning a radiation emitter movably supported by a first support structure along a first annular pathway, and a radiation detector movably supported by a second support structure along a second annular pathway, such that a radiation beam stretches between the radiation emitter and the radiation detector;
determining the spatial position of a radiation beam stretching between the radiation emitter and the radiation detector;
acquiring an image via a camera which is positionally coupled to and moving together with either the radiation emitter or the radiation detector, and is oriented towards an area surrounded by the first and the second pathway;
creating an AR-image based on the image received from the camera and an AR-overlay which contains at least one of the following:
a radioscopic-image obtained from the radiation detector, particularly a currently acquired and/or a previously acquired radioscopic-image of the patient;
a reconstructed-radioscopic-image calculated from currently acquired and/or previously acquired radioscopic-images of the patient;
a 2D-image of the patient;
a 3D-image-dataset of the patient;
a 2D-image calculated from a 3D-image-dataset of the patient;
a virtual 2D- or 3D-representation of anatomical structures of the patient, particularly of pathological structures of the patient;
a virtual 2D- or 3D-representation of a predefined planning geometry, which in particular contains a trajectory, a target point and/or an entry point for an instrument;
a virtual representation of the field-of-view of the imaging unit comprising the radiation emitter and the radiation detector;
a virtual representation of the radiation beam;
a virtual representation of an area of the patient's skin and/or a volume of the patient's body that is intersected by the radiation beam.

A further aspect of, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. In case a method step requires a physical object to be moved or otherwise manipulated, the computer is adapted to control one or more powered actuators, which are adopted to move or manipulate the one or more objects in the desired manner. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program.

A further aspect of the invention is directed to a non-transitory computer-readable program storage medium on which the program according to the second aspect is stored.

A further aspect of the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

The invention does not involve or in particular comprise or encompass an invasive step which would represent a substantial physical interference with the body requiring professional medical expertise to be carried out and entailing a substantial health risk even when carried out with the required professional care and expertise.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The n-dimensional image of a body is registered when the spatial location of each point of an actual object within a space, for example a body part in an operating theatre, is assigned an image data point of an image (CT, MR, etc.) stored in a navigation system.

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

The information on the imaging geometry preferably comprises information which allows the analysis image (x-ray image) to be calculated, given a known relative position between the imaging geometry analysis apparatus and the analysis object (anatomical body part) to be analyzed by x-ray radiation, if the analysis object which is to be analyzed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made for example to the following publications:

1. "An Efficient and Accurate Camera Calibration Technique for 3D Machine Vision", Roger Y. Tsai, Proceedings of the IEEE Conference on Computer Vision and Pattern Recognition. Miami Beach, Fla., 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344.
3. "Fluoroscopic X-ray Image Processing and Registration for Computer-Aided Orthopedic Surgery", Ziv Yaniv
4. EP 08 156 293.6
5. U.S. 61/054,187

Shape representatives represent a characteristic aspect of the shape of an anatomical structure. Examples of shape representatives include straight lines, planes and geometric figures. Geometric figures can be one-dimensional such as for example axes or circular arcs, two-dimensional such as for example polygons and circles, or three-dimensional such as for example cuboids, cylinders and spheres. The relative position between the shape representatives can be described in reference systems, for example by co-ordinates or vectors, or can be described by geometric variables such as for example length, angle, area, volume and proportions. The characteristic aspects which are represented by the shape representatives are for example symmetry properties which are represented for example by a plane of symmetry. Another example of a characteristic aspect is the direction of extension of the anatomical structure, which is for example represented by a longitudinal axis. Another example of a characteristic aspect is the cross-sectional shape of an anatomical structure, which is for example represented by an ellipse. Another example of a characteristic aspect is the surface shape of a part of the anatomical structure, which is for example represented by a plane or a hemisphere. For example, the characteristic aspect constitutes an abstraction of the actual shape or an abstraction of a property of the actual shape (such as for example its symmetry properties or longitudinal extension). The shape representative for example represents this abstraction.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

The movements of the treatment body parts are for example due to movements which are referred to in the following as "vital movements". Reference is also made in this respect to EP 2 189 943 A1 and EP 2 189 940 A1, also published as US 2010/0125195 A1 and US 2010/0160836 A1, respectively, which discuss these vital movements in detail. In order to determine the position of the treatment body parts, analytical devices such as x-ray devices, CT devices or MRT devices are used to generate analytical images (such as x-ray images or MRT images) of the body. For example, analytical devices are constituted to perform medical imaging methods. Analytical devices for example use medical imaging methods and are for example devices for analyzing a patient's body, for instance by using waves and/or radiation and/or energy beams, for example electromagnetic waves and/or radiation, ultrasound waves and/or particles beams. Analytical devices are for example devices which generate images (for example, two-dimensional or three-dimensional images) of the patient's body (and for example of internal structures and/or anatomical parts of the patient's body) by analyzing the body. Analytical devices are for example used in medical diagnosis, for example in radiology. However, it can be difficult to identify the treatment body part within the analytical image. It can for example be easier to identify an indicator body part which correlates with changes in the position of the treatment body part and for example the movement of the treatment body part.

Tracking an indicator body part thus allows a movement of the treatment body part to be tracked on the basis of a known correlation between the changes in the position (for example the movements) of the indicator body part and the changes in the position (for example the movements) of the treatment body part. As an alternative to or in addition to tracking indicator body parts, marker devices (which can be used as an indicator and thus referred to as "marker indicators") can be tracked using marker detection devices. The position of the marker indicators has a known (predetermined) correlation with (for example, a fixed relative position relative to) the position of indicator structures (such as the thoracic wall, for example true ribs or false ribs, or the diaphragm or intestinal walls, etc.) which for example change their position due to vital movements.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumor represents an example of a change in an anatomical structure. If the tumor grows, it may then be said to represent an expanded anatomical structure. This expanded anatomical structure may not be detectable; for example, only a part of the expanded anatomical structure may be detectable. Primary/high-grade brain tumors are for example usually visible on MRI scans when contrast agents are used to infiltrate the tumor. MRI scans represent an example of an imaging method. In the case of MRI scans of such brain tumors, the signal enhancement in the MRI images (due to the contrast agents infiltrating the tumour) is considered to represent the solid tumor mass. Thus, the tumor is detectable and for example discernible in the image generated by the imaging method. In addition to these tumors, referred to as "enhancing" tumors, it is thought that approximately 10% of brain tumors are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimization algorithms are applied in order to find the transformation which results in an optimum degree of similarity. The degree of similarity is preferably measured by way of a measure of similarity (also referred to in the following as a "similarity measure"). The parameters of the optimization algorithm are for example vectors of a deformation field. These vectors are determined by the optimization algorithm in such a way as to result in an optimum degree of similarity. Thus, the optimum degree of similarity represents a condition, for example a constraint, for the optimization algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimizing problem is for example solved iteratively, for example by means of an optimization algorithm which is for example a first-order optimization algorithm, such as a gradient descent algorithm. Other examples of optimization algorithms include optimization algorithms which do not use derivations, such as the downhill simplex algorithm, or algorithms which use higher-order derivatives such as Newton-like algorithms. The optimization algorithm preferably performs a local optimization. If there is a plurality of local optima, global algorithms such as simulated annealing or generic algorithms can be used. In the case of linear optimization problems, the simplex method can for instance be used.

In the steps of the optimization algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighboring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

A medical workflow comprises a plurality of workflow steps performed during a medical treatment and/or a medical diagnosis. The workflow steps are typically, but not necessarily performed in a predetermined order. Each workflow step for example means a particular task, which might be a single action or a set of actions. Examples of workflow steps are capturing a medical image, positioning a patient, attaching a marker, performing a resection, moving a joint, placing an implant and the like.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
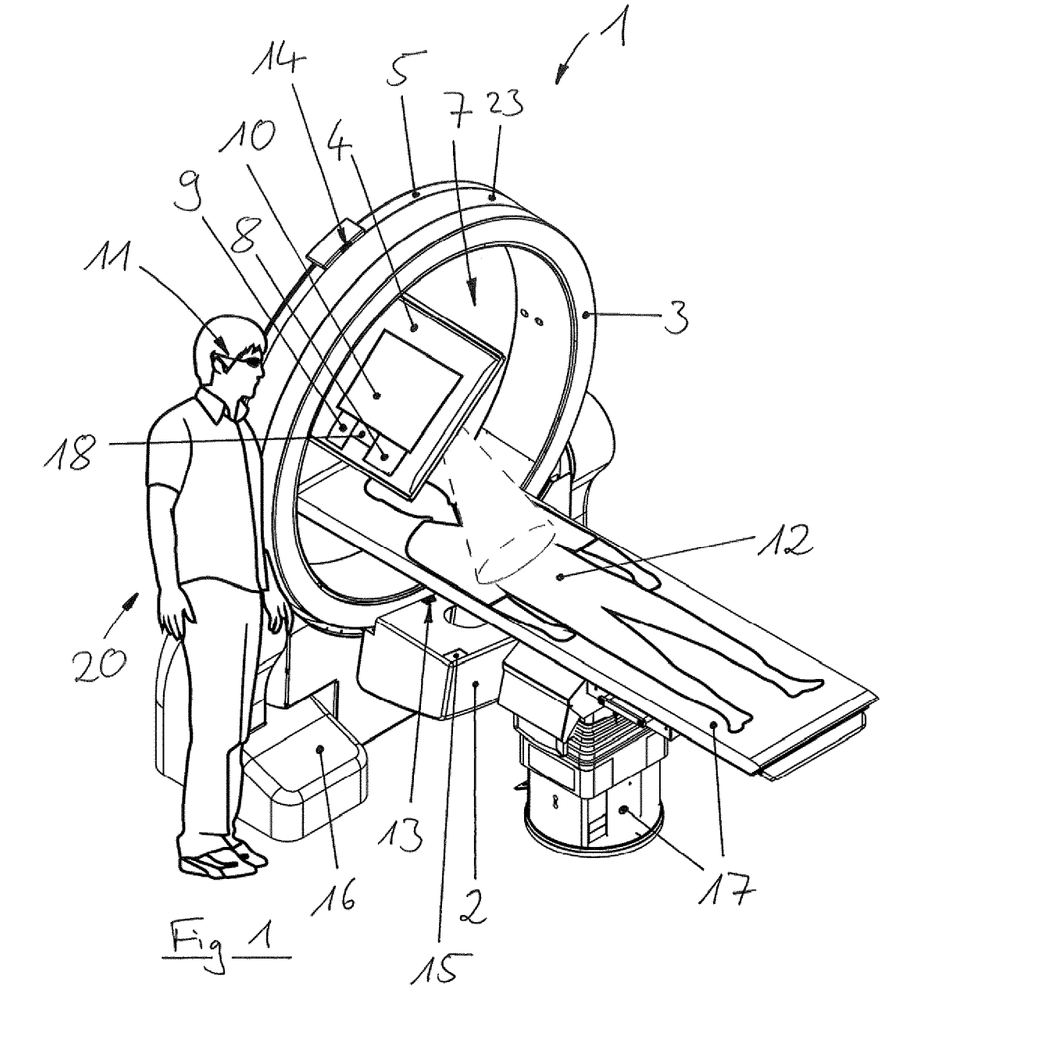
FIG. 1 shows an embodiment of an imaging apparatus in accordance with the present invention.

FIG. 1 shows an embodiment of the inventive imaging device 1 which is already positioned with respect to a patient table 17 with a patient 12 lying thereon. The imaging device 1 comprises two concentric and ring-shaped support structures 3 and 5, which carry a radiation emitter 2 and a radiation detector 4, respectively. Support rings 3 and 5 can rotate independently from each other around a common axis of rotation as they are rotatably connected to a static ring-shaped basis 23 which is in turn rotatably carried by the undercarriage 16 around a horizontal axis (not indicated).

By moving the support rings 3 and 5, the radiation emitter 2 and the radiation detector 4 are respectively moved around the patient 12. While the radiation emitter 2 is connected to the support ring 3, the radiation detector 4 is connected to the support ring 5. Further, the spatial position of the radiation emitter 2 and radiation detector 4 with respect to each other can be determined via the sensors 13 and 14 which detect the respective angular positions around the basis 23. As soon as the radiation emitter 2 and the radiation detector 4 have reached a desired position with respect to the patient 12 and with respect to each other so as to take one or more radioscopic images of the patient 12, a user 20 may verify the correct setup of the imaging apparatus 1 by looking at display 10. Display 10 shows an AR-image which basically consists, on the first hand, of a camera image obtained via a camera 6 which is disposed at the opposite side of the housing of the radiation detector 4, and which is directed towards the volume 7 with the patient 12 and surrounded by rings 3 and 5. On the other hand, the AR-image comprises an AR-overlay that is superimposed over the camera image. In this specific example, the AR-overlay may visually indicate the field of view provided by the current setup of the radiation emitter 2 and the radiation detector 4 with respect to the anatomy of the patient 12. In order to superimpose the AR-overlay correctly over the camera image, the position determination module 8 receives signals not only from the position sensors 13 and 14, but also from the sensor 15 which determines the shape of the collimator (not shown) of the radiation emitter 2. On the basis of the received signals, the position determination module 8 is able to determine the spatial position of the radiation beam. Since the camera 6 has a spatially invariant position with respect to the radiation detector 4, the position determination module 8 is also able to determine the spatial position of the radiation beam within the field of view of the camera 6.

The AR-visualization module 9 is operably coupled to both, the camera 6 and the position determination module 8 and is adapted to create the AR-image on the basis of the camera image and the AR-overlay in a spatially correct alignment.

The obtained AR-image is then transmitted from the AR-visualization module to a display interface 18 which, for the shown embodiment, has a wired connection to the display 10 and a wireless connection to the AR-spectacles 11 worn by the user 20. Thus, the user 20 can have a look at the provided AR-image on either the display 10 or the AR-spectacles 11.

Figure 2:
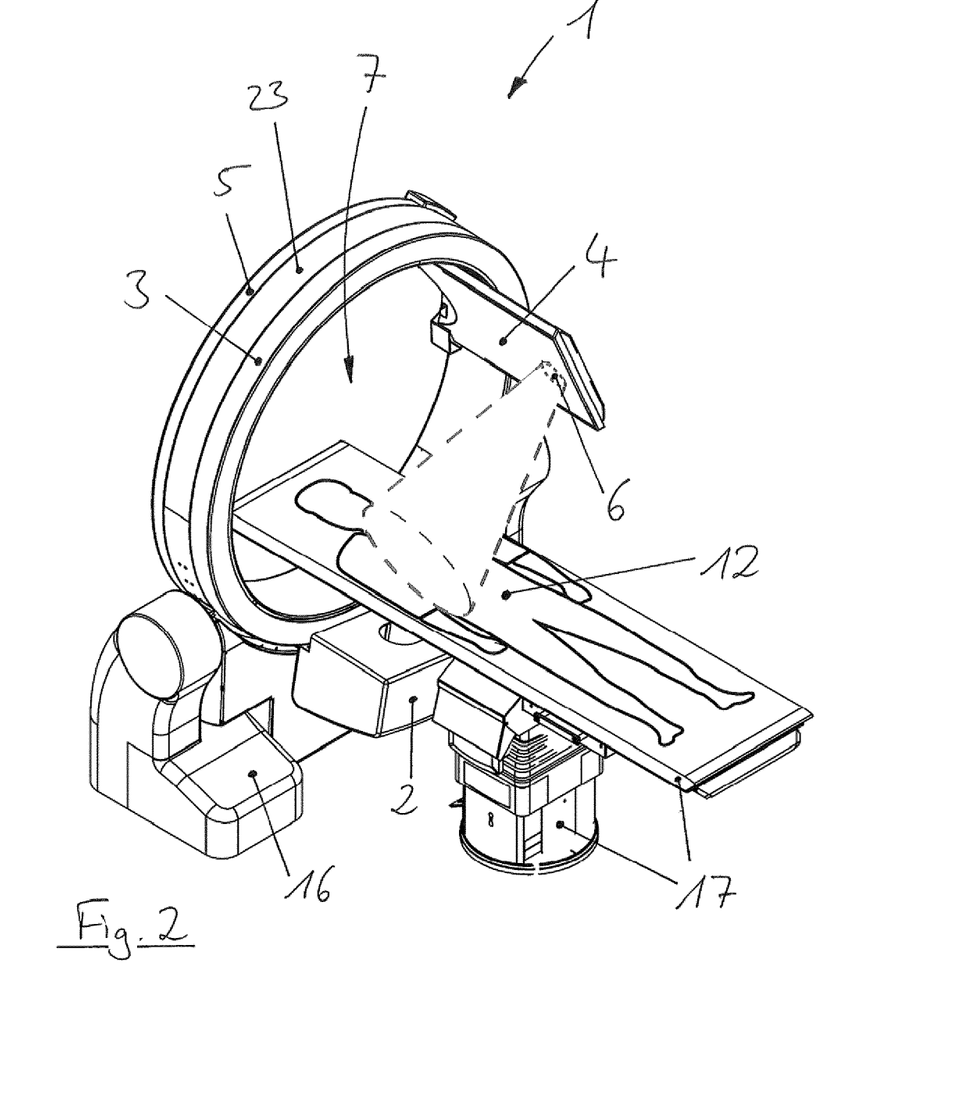
FIG. 2 shows the imaging apparatus of FIG. 1.

FIG. 2 shows the embodiment of FIG. 1, wherein the radiation detector 4 is moved together with 6 and the display 10 around its angular pathway towards the other side of the patient 12 and the patient support 17. In the setup shown in FIG. 2, the radiation emitter 2 remains in its lowermost position underneath the patient support 17.

Figure 3:
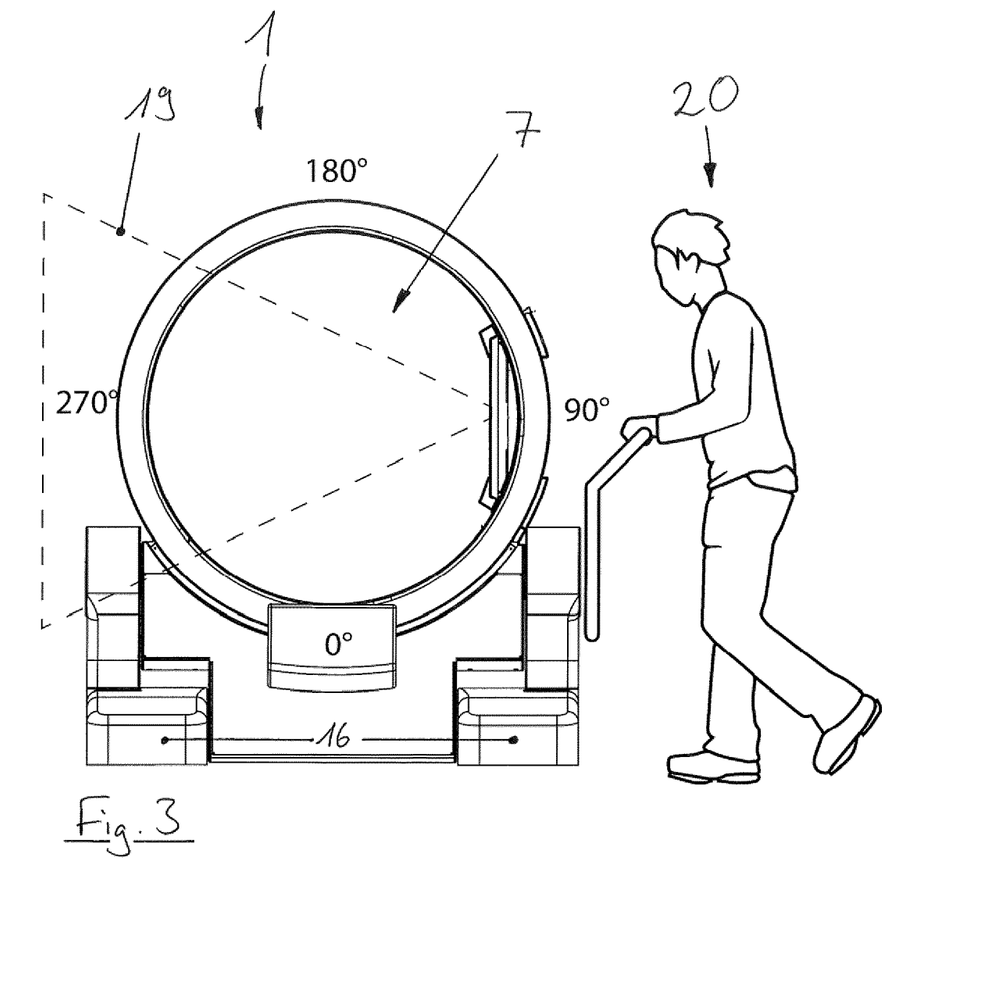
FIG. 3 shows the imaging apparatus of FIGS. 1 and 2 in a transport configuration.

FIG. 3 shows the embodiment of FIG. 1 in a transport position, wherein the radiation detector 4 is rotated to a side position such that both, the display 10 and the camera 6 are oriented horizontally. In this position, the camera 6 provides a camera image which covers the area 19 "in front of" the imaging device 1 which is not viewable by the user 20 who pushes the imaging device 1 in a forward direction. Since the display 10 is oriented horizontally, it is easy to look at for the user 20.

Figure 4:
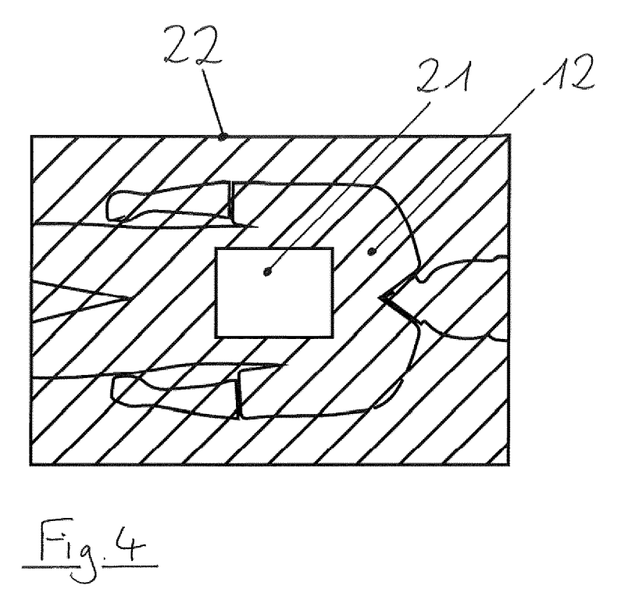
FIG. 4 shows a schematic depiction of an uncovered surgical site.

FIG. 4 schematically shows a patient 12 who is covered for surgery with a surgical drape 22. The surgical site 21 itself is left uncovered. Within a camera image provided by the camera 6, the surgical site can be identified by means of known image detection measures, such that the radiation beam generated by the radiation emitter 2 can be shaped and oriented with respect to the patient 12 in accordance with the detected orientation and shape of the surgical site 21.

Figure 5:
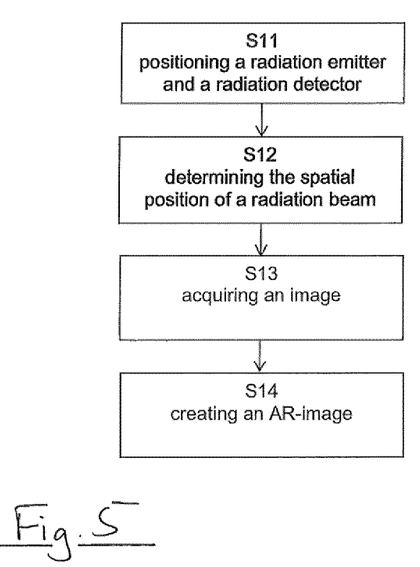
FIG. 5 shows the basic steps of a method in accordance with the present invention.

FIG. 5 shows the basic steps of the method in accordance with the present invention. In a first step S11, the radiation emitter 2 and the radiation detector 4 are positioned in a desired manner with respect to a patient 12 and with respect to each other. In a following step S12, the spatial position (spatial location and/or spatial orientation) of the radiation beam which stretches between the radiation emitter 2 and the radiation detector 4 is determined. Further, a camera image is acquired in step S13. Based on the spatial position of the radiation beam and the acquired camera image, an AR-image is created in step S14.

The invention claimed is:
1. A medical imaging apparatus, comprising:
a radiation emitter movably supported by a first support structure along a first annular pathway;
a radiation detector movably supported by a second support structure along a second annular pathway;
a camera positionally coupled to and moving together with either the radiation emitter or the radiation detector, and oriented towards an area surrounded by the first and the second pathway;
a position determination module adapted to determine the spatial position of a radiation beam stretching between the radiation emitter and the radiation detector;
an AR-visualization module operably coupled to the camera Band to the position determination module, which is adapted to create an AR-image based on an image received from the camera and an AR-overlay positionally registered with the image, and which includes a display interface adapted to transmit the created AR-image to a medical display,
wherein the AR-overlay comprises a virtual representation of the field-of-view of the imaging apparatus comprising the radiation emitter and the radiation detector.

2. The medical imaging apparatus according to claim 1, wherein the AR-overlay comprises at least one of the following:
a radioscopic-image obtained from the radiation detector;
a reconstructed-radioscopic-image calculated from currently acquired and/or previously acquired radioscopic-images of the patient;
a 2D-image of the patient;
a 3D-image-dataset of the patient;
a 2D-image calculated from a 3D-image-dataset of the patient;
a virtual 2D- or 3D-representation of anatomical structures of a patient;
a virtual 2D- or 3D-representation of a predefined planning geometry;
a virtual representation of the radiation beam;
a virtual representation of an area of the patient's skin and/or a volume of the patient's body that is intersected by the radiation beam.

3. The medical imaging apparatus according to claim 1, wherein the radiation emitter and the radiation detector allow for eccentric imaging by being movably supported in a manner independent from each other.

4. The medical imaging apparatus according to claim 3, wherein the first support structure and the second support structure are formed by a first support ring and a second support ring, respectively.

5. The medical imaging apparatus according to claim 1, wherein the position determination module is operably connected to at least one of the following:
at least one first position sensor for determining the spatial position of the radiation emitter;
at least one second position sensor for determining the spatial position of the radiation detector;
at least one sensor adapted to sense the shape of a collimator assigned to the radiation emitter.

6. The medical imaging apparatus according to claim 1, further comprising an undercarriage having a plurality of wheels, which allows the imaging apparatus to move over the ground.

7. The medical imaging apparatus according to claim 1, further comprising one or more display devices connected to the display interface, wherein at least one of the display devices is:
positionally coupled to and moving together with either the radiation emitter or the radiation detector, and oriented away from the area surrounded by the first and the second pathway;
freely movable with respect to the medical imaging apparatus.

8. The medical imaging apparatus according to claim 6, wherein the medical imaging apparatus is adapted to be transferred into a transport configuration, in which the display interface transmits an image showing an area of an operator's field of view that is obscured by the imaging apparatus during transport.

9. The medical imaging apparatus according to claim 8, wherein the display is moved together with either the radiation emitter or the radiation detector to a substantially horizontally position to show the area of the operator's field of view that is obscured by the imaging apparatus during transport to the operator.

10. The medical imaging apparatus according to claim 1, wherein the AR-visualisation module creates an AR-image with the AR-overlay containing information for assisting in moving the medical imaging apparatus.

11. The medical imaging apparatus according to claim 1, adapted to control an initial size, initial shape and/or initial spatial position of the radiation beam in accordance with a pattern recognition procedure performed on an image that is provided by the camera.

12. A method comprising:
determining, using a position determination module, the spatial positon of a radiation beam stretching between a radiation emitter and a radiation detector, the radiation emitter being movably supported by a first support structure along a first annular pathway and the radiation detector being movably supported by a second support structure along a second annular pathway;
acquiring an image via a camera that is positionally coupled to and moving together with either the radiation emitter or the radiation detector and oriented towards an area surrounded by the first and the second pathway;
creating, using an AR-visualization module operably coupled to a camera and to the position determination module, an AR-image based on the image acquired from the camera and an AR-overlay positionally registered with the image, wherein the AR-overlay comprises a virtual representation of the field-of-view of an imaging unit comprising the radiation emitter and the radiation detector; and
presenting the AR-image that is based on the image received from the camera and the AR-overlay.

13. The method according to claim 12, comprising the steps of:
positioning the radiation emitter along the first annular pathway, and the radiation detector along the second annular pathway, such that the radiation beam stretches between the radiation emitter and the radiation detector.

14. A program, logic stored in a memory device of a computer that when running on the computer or when loaded onto the computer, causes the computer to perform a method; comprising:
determining, using a position determination module, the spatial positon of a radiation beam stretching between a radiation emitter and a radiation detector, the radiation emitter being movably supported by a first support structure along a first annular pathway and the radiation detector being movably supported by a second support structure along a second annular pathway;
acquiring an image via a camera that is positionally coupled to and moving together with either the radiation emitter or the radiation detector and oriented towards an area surrounded by the first and the second pathway;
creating, using an AR-visualization module operably coupled to a camera and to the position determination module, an AR-image based on the image acquired from the camera and an AR-overlay positionally registered with the image, wherein the AR-overlay comprises a virtual representation of the field-of-view of an imaging unit comprising the radiation emitter and the radiation detector; and
presenting the AR-image that is based on the image received from the camera and the AR-overlay.

15. The method according to claim 13, wherein the AR-overlay contains at least one of the following:
- a radioscopic-image obtained from the radiation detector;
- a reconstructed-radioscopic-image calculated from currently acquired and/or previously acquired radioscopic-images of the patient;
- a 2D-image of the patient;
- a 3D-image-dataset of the patient;
- a 2D-image calculated from a 3D-image-dataset of the patient;
- a virtual 2D- or 3D-representation of anatomical structures of the patient;
- a virtual 2D- or 3D-representation of a predefined planning geometry;
- a virtual representation of the radiation beam;
- a virtual representation of an area of the patient's skin and/or a volume of the patient's body that is intersected by the radiation beam.

16. The medical imaging apparatus according to claim 2, wherein the radioscopic-image obtained from the radiation detector is a currently acquired and/or a previously acquired radioscopic-image, wherein the virtual 2D- or 3D-representation of anatomical structures of a patient are of pathological structures of the patient, and/or wherein the virtual 2D- or 3D-representation of a predefined planning geometry contains a trajectory, a target point and/or an entry point for an instrument.

17. The medical imaging apparatus according to claim 4, wherein the first and second support rings are rotatable around a common axis of rotation.

18. The medical imaging apparatus according to claim 6, wherein the wheels allow the imaging apparatus to move with respect to a patient table provided separately to the medical imaging apparatus.

19. The medical imaging apparatus according to claim 7, wherein the freely movable display device comprises AR-spectacles.

20. The medical imaging apparatus according to claim 10, wherein the information includes dimensions of the medical imaging apparatus in a moving direction and/or a distance of an obstacle to the medical imaging apparatus.

* * * * *